US011830078B2

(12) United States Patent
Hibbert-Iacobacci et al.

(10) Patent No.: US 11,830,078 B2
(45) Date of Patent: Nov. 28, 2023

(54) METHODS FOR ELECTRONICALLY PROCESSING INSURANCE CLAIMS AND DEVICES THEREOF

(71) Applicant: Mitchell International, Inc., San Diego, CA (US)

(72) Inventors: Michele Hibbert-Iacobacci, Ramona, CA (US); Valerie Lindgren, San Diego, CA (US); Vicki Dunbar, San Diego, CA (US); Susan Englehart, San Diego, CA (US)

(73) Assignee: Mitchell International, Inc., San Diego, CA (US)

( * ) Notice: Subject to any disclaimer, the term of this patent is extended or adjusted under 35 U.S.C. 154(b) by 0 days.

(21) Appl. No.: 17/546,005

(22) Filed: Dec. 8, 2021

(65) Prior Publication Data
US 2022/0101447 A1    Mar. 31, 2022

Related U.S. Application Data

(63) Continuation-in-part of application No. 16/678,216, filed on Nov. 8, 2019, now abandoned.

(60) Provisional application No. 62/758,185, filed on Nov. 9, 2018.

(51) Int. Cl.
*G06N 20/00*  (2019.01)
*G06Q 40/08*  (2012.01)
*G16H 10/60*  (2018.01)

(52) U.S. Cl.
CPC .............. *G06Q 40/08* (2013.01); *G16H 10/60* (2018.01); *G06N 20/00* (2019.01)

(58) Field of Classification Search
None
See application file for complete search history.

(56) References Cited

U.S. PATENT DOCUMENTS

| 10,140,421 | B1* | 11/2018 | Bernard | G06V 10/764 |
| 2014/0040249 | A1* | 2/2014 | Ploesser | G06Q 10/10 |
| | | | | 707/723 |
| 2015/0331995 | A1* | 11/2015 | Zhao | G16H 50/20 |
| | | | | 705/2 |
| 2015/0379241 | A1* | 12/2015 | Furst | G16H 10/60 |
| | | | | 705/3 |
| 2021/0342946 | A1* | 11/2021 | Leise | G06Q 20/4015 |

FOREIGN PATENT DOCUMENTS

CN        110335676 A  * 10/2019

* cited by examiner

*Primary Examiner* — Xuyang Xia
(74) *Attorney, Agent, or Firm* — Sheppard Mullin Richter & Hampton LLP

(57) ABSTRACT

A method and computing apparatus for automatically identifying whether or not one or more identified injuries are related to the insurance claim which has been submitted is described. The method and computing apparatus identify injury data in an electronic medical claim data associated with a claimant based diagnosis code data, uses a classifier to determine an association between the identified injury data represented by the diagnosis code data and the initial injury data represented by the initial diagnosis code data is identified when historical claim data is determined to be present for the claimant.

18 Claims, 7 Drawing Sheets

| ICD-10 Code | Description |
|---|---|
| B053 | Measles complicated by otitis media |
| H6501 | Acute serous otitis media, right ear |
| H65113 | Acute and subacute allergic otitis media (mucoid) (sanguineous) (serous), bilateral |
| H65194 | Other acute nonsuppurative otitis media, recurrent, right ear |
| H6532 | Chronic mucoid otitis media, left ear |
| H66012 | Acute suppurative otitis media with spontaneous rupture of ear drum, left ear |
| H6613 | Chronic tubotympanic suppurative otitis media, bilateral |
| H6622 | Chronic atticoantral suppurative otitis media, left ear |
| J1183 | Influenza due to unidentified influenza virus with otitis media |

FIG. 5

METHODS FOR ELECTRONICALLY PROCESSING INSURANCE CLAIMS AND DEVICES THEREOF

RELATED APPLICATIONS

This application a continuation-in-part of U.S. patent application Ser. No. 16/678,216, filed on Nov. 8, 2019, which claims the benefit of U.S. Provisional Application No. 62/758,185 filed on Nov. 9, 2018, the contents of which are incorporated herein by reference in its entirety.

BACKGROUND

To assist with managing insurance claims, various types of coding systems have evolved to communicate claim related information in a nationally accepted common format that is readable by electronic claims payment systems. One of these coding systems is the International Classifications of Diseases (ICD) code system which provides codes that identify what service has been provided along with the diagnosis, symptom, complaint, condition or problem as well as the particular resources used.

Unfortunately, existing technological solutions for processing these codes when managing insurance claims are typically limited to simply providing these claims with the codes electronically, and provide little further assistance, thus, there is still heavy reliance on manual analysis of the underlying claim and code(s). In particular, these received claims often contain codes developed for different applications and purposes which do not transfer properly when assessing an insurance claim. Additionally, these received claims contain claim related data in addition to these codes which simply on their face fail to provide sufficient information to accurately and consistently identify whether or not one or more identified injuries are related to the insurance claim which has been submitted. This lack of any technological tools to accurately and consistently assess these claims with this uncorrelated data and codes designed for other purposes, results in errors and inconsistencies and thus inappropriate reimbursements.

SUMMARY

In accordance with one or more embodiments, various features and functionality are provided to automatically identify whether or not one or more identified injuries are related to the insurance claim which has been submitted.

Other features and aspects of the disclosed technology will become apparent from the following detailed description, taken in conjunction with the accompanying drawings, which illustrate, by way of example, the features in accordance with embodiments of the disclosed technology. The summary is not intended to limit the scope of any inventions described herein, which are defined solely by the claims attached hereto.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

FIG. 5 an example block diagram of injuries represented by the diagnosis code and the corresponding textual description of the injury, according to an implementation of the disclosure.

Described herein are systems and methods for improving the process configured to automatically identify whether or not one or more identified injuries are related to the insurance claim which has been submitted. The details of some example embodiments of the systems and methods of the present disclosure are set forth in the description below. Other features, objects, and advantages of the disclosure will be apparent to one of skill in the art upon examination of the following description, drawings, examples and claims. It is intended that all such additional systems, methods, features, and advantages be included within this description, be within the scope of the present disclosure, and be protected by the accompanying claims.

DETAILED DESCRIPTION

As alluded to above, currently existing solutions fail to automatically identify whether or not one or more identified injuries are related to the insurance claim which has been submitted for processing. Accordingly, the present process is configured to use uncorrelated data and codes designed for other purposes (e.g., various claim related data elements, diagnosis codes and/or injury codes, and historic data related to previously correlated injuries to determine relatedness of the injury to the claim. The machine learning algorithm may be trained using data that was previously compiled by data analysts (experts) to determine direct clinical correlation between the injury in the received electronic medical claim and the injury present in the historical medical claim.

In some embodiments, the system and method may be configured to provide a streamlined claim processing functionality, having little to no human interaction, an enhanced manual clinical review, when needed, and a process for fraud detection.

Figure 1:
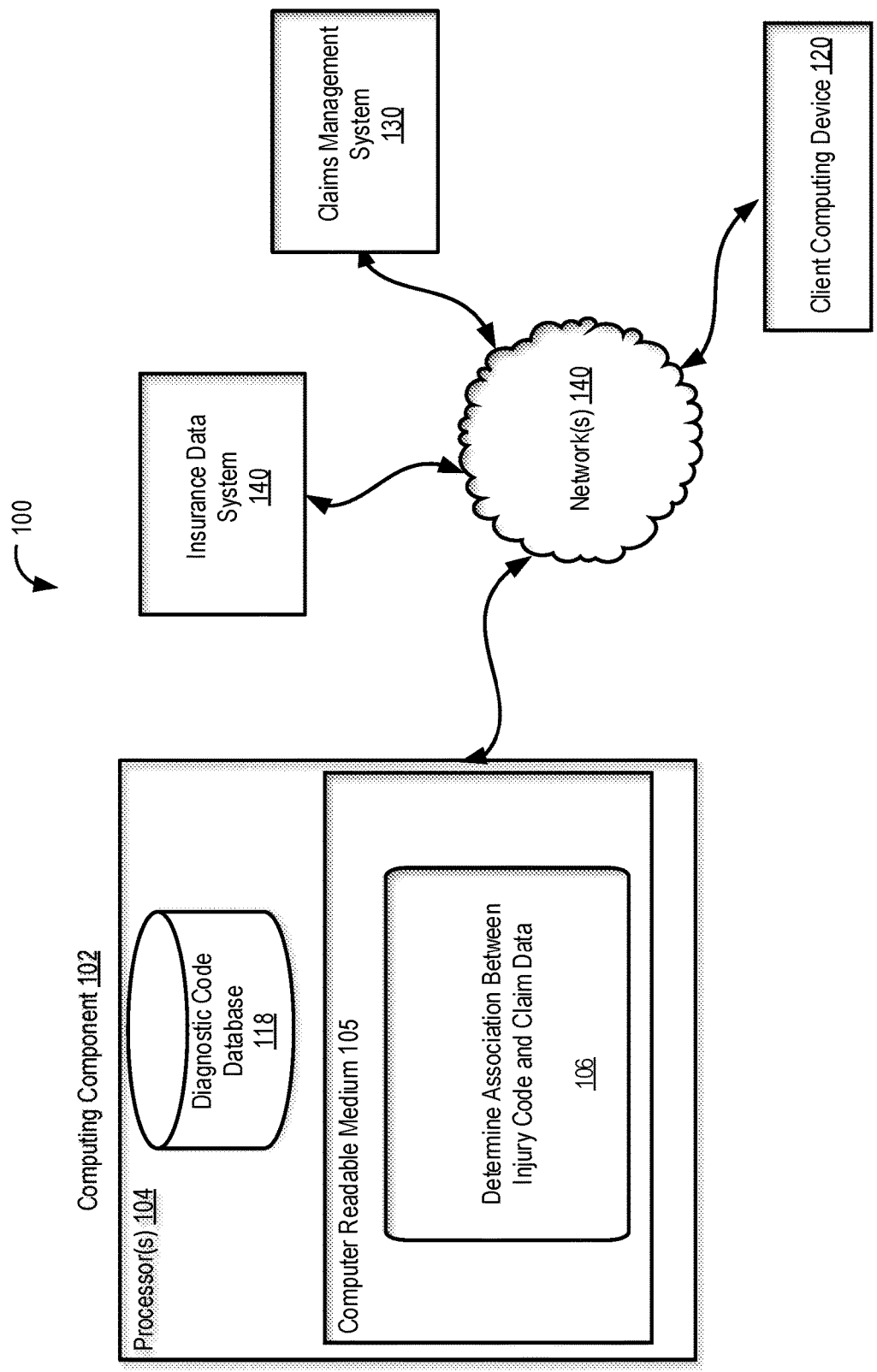
FIG. 1 illustrates a claim processing system, according to an implementation of the disclosure.

FIG. 1 illustrates a claim processing system 100, in accordance with the embodiments disclosed herein. This diagram illustrates an example system 100 that may include a computing component 102 in communication with a network 140. The system 100 may also include one or more external resources 130 and a client computing device 120 that are in communication with network 140. External resources 130 may be located in a different physical or geographical location from the computing component 102.

As illustrated in FIG. 1, computing component or device 102 may be, for example, a server computer, a controller, or any other similar computing component capable of processing data. In the example implementation of FIG. 1, computing component 102 includes a hardware processor 104 configured to execute one or more instructions residing in a machine-readable storage medium 105 comprising one or more computer program components.

Hardware processor 104 may be one or more central processing units (CPUs), semiconductor-based microprocessors, and/or other hardware devices suitable for retrieval and execution of instructions stored in computer readable medium 105. Processor 104 may fetch, decode, and execute instructions 106-112, to control processes or operations for determining injury relatedness. As an alternative or in addition to retrieving and executing instructions, hardware processor 104 may include one or more electronic circuits that include electronic components for performing the functionality of one or more instructions, such as a field programmable gate array (FPGA), application specific integrated circuit (ASIC), or other electronic circuits.

A computer readable storage medium, such as machine-readable storage medium 105 may be any electronic, magnetic, optical, or other physical storage device that contains or stores executable instructions. Thus, computer readable storage medium 105 may be, for example, Random Access Memory (RAM), non-volatile RAM (NVRAM), an Electrically Erasable Programmable Read-Only Memory (EEPROM), a storage device, an optical disc, and the like. In some embodiments, machine-readable storage medium 105 may be a non-transitory storage medium, where the term "non-transitory" does not encompass transitory propagating signals. As described in detail below, machine-readable storage medium 105 may be encoded with executable instructions, for example, instructions 106.

Method

Figure 2:
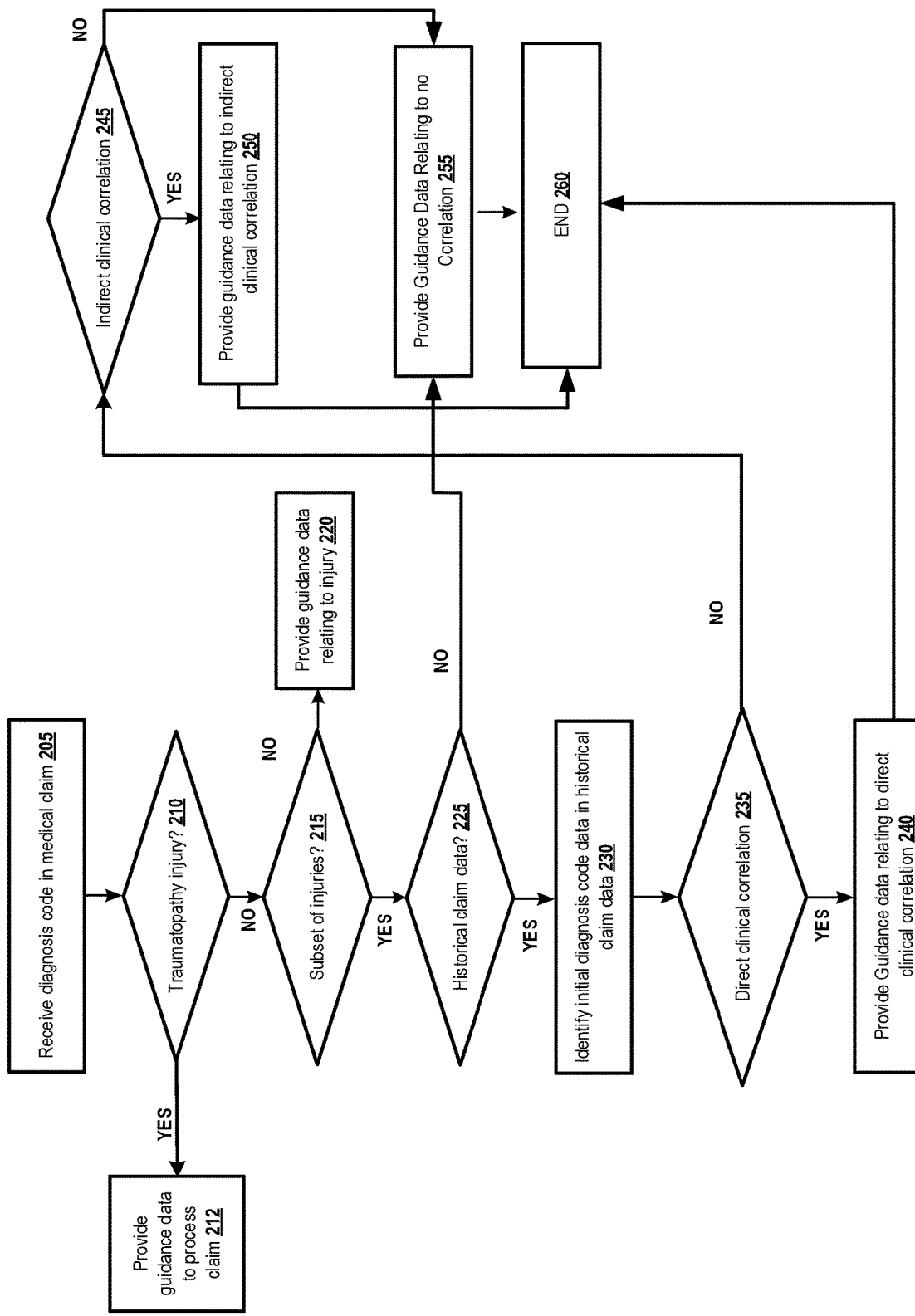
FIG. 2 illustrates an example method for electronically processing insurance claims, according to an implementation of the disclosure.

FIG. 2 illustrates an example process for electronically processing insurance claims and for automatically determining the correlation between the injury code and the claim. In particular, the system is configured to utilize proprietary data that identifies migrating diagnoses. Migrating diagnoses are diagnosis codes used by providers that may be unrelated to the injury but are nonetheless submitted as part of the insurance claim.

At step 205, an electronic medical bill of a patient is received. For example, from a claims management system. In this example, the received medical bill includes claim data associated with the one or more injuries and their corresponding initial diagnosis code along with the injury data indicating the level of severity of the injuries, although the medical bill can include other types or amounts of information.

Figure 4:
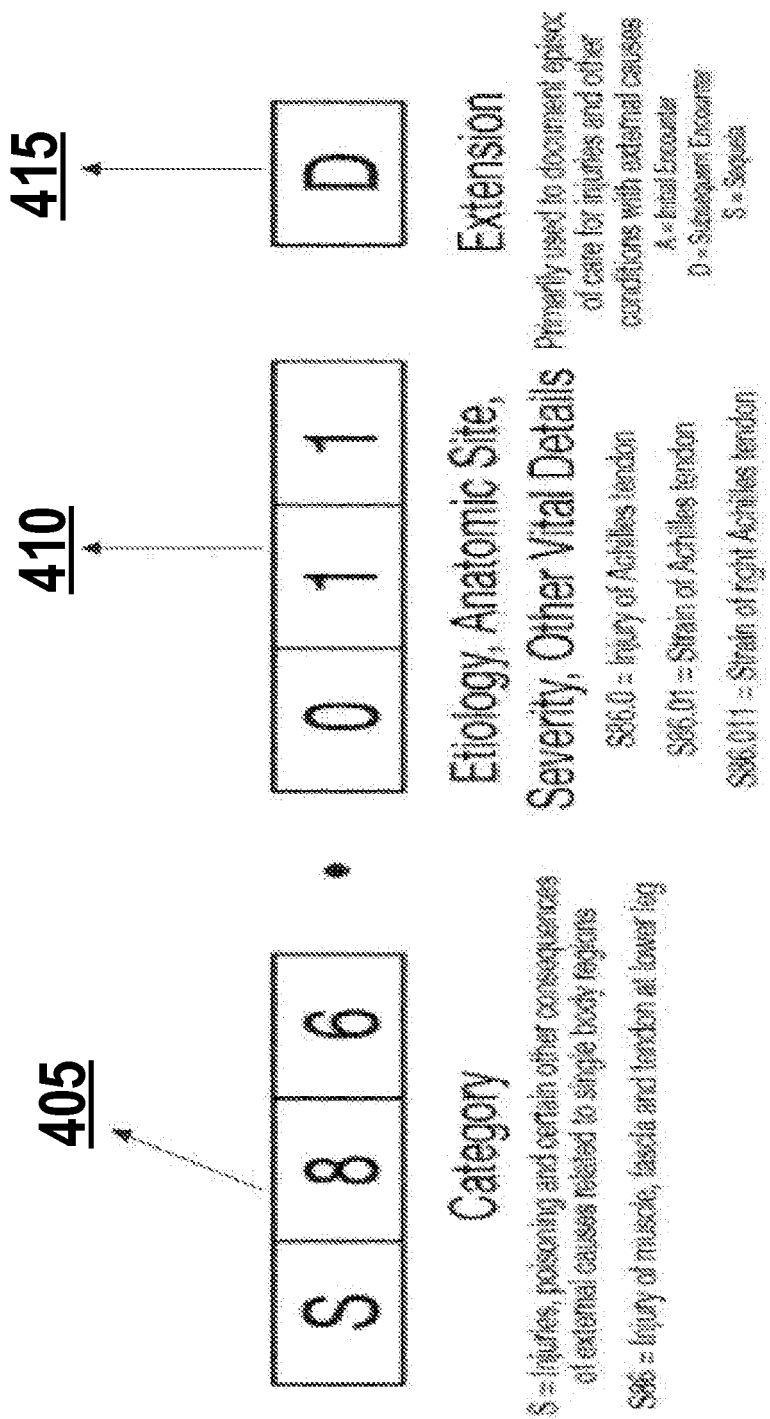
FIG. 4 illustrates an example medical claim data relating to a nature of an injury, a diagnosis code, and a level of severity of the injury, according to an implementation of the disclosure.

One example of the initial diagnosis code along with the level of severity of the injury is illustrated in FIG. 4. By way of example, if the initial diagnosis code is S86.011.D, then the category 405 describes S86 as the injury, poisoning and certain other consequences of external causes related to single body regions. The next three numeric values 410 represents the etiology, anatomic site, severity, and other vital details. By way of example, a lower numeric value can indicate a lower severity level, a higher numeric value can indicate higher severity level and in between the lower numeric value and the higher numeric value can indicate medium severity, although in other examples, lower severity level of the injury can be represented by a higher numeric value and the higher severity level can be represented by a lower numeric value. For purpose of further illustration, if the range of the numeric value is between 0-3, then the severity level could be low; if the range of the numeric value is between 4-6, then the severity level could be medium; and for a range of the numeric value between 7-9, the severity level can be high. Finally, the last character 415 represents the extension that is primarily used to document episode of care for injuries and other conditions with external causes. For example, "A" indicates that injury is from an initial encounter, "D" indicates that injury is from a subsequent encounter, and S indicates is sequela.

Referring back to FIG. 2, upon receiving the electronic medical claim, the claim processing system extracts the diagnosis code from the electronic medical claim. In this example, the electronic medical claim includes a data field with name diagnosis code for each of the injury identified in the electronic claim and the claim processing system extracts the alpha-numeric characters present within the diagnosis code field of the electronic medical claim, although other techniques can be used to identify and extract the diagnosis code from the electronic medical claim. Further, the claim processing system extracts the severity indicator from the extracted diagnosis code.

As illustrated above, the severity indicator is the third numeric value from left of the numeric values 410 illustrated in FIG. 4, although other types or amounts of information within the diagnosis code can provide the severity indicator.

In step 210, the claim processing system determines whether the injury in the received electronic medical claim is a traumatopathic injury by correlating at least the first three characters of the extracted diagnosis against the description of the injury stored in a table within the diagnosis code database (e.g., database 118 in FIG. 1), although the claim processing system can use other techniques to determine when the injury is a traumatopathic injury. In this example, traumatopathic injury relates to pathologic condition resulting from violence or wounds. For example, as illustrated in FIG. 5, the diagnosis code and the corresponding description of the injury which is stored within the diagnosis code database 118. Accordingly, when the claim processing system determines that the injury in the received electronic medical claim is a traumatopathic injury, then the "Yes" branch is taken to step 212, as illustrated in FIG. 2.

In step 212, the claim processing system provides the guidance data to process the received electronic medical claim to the requesting claims management system 130. Optionally, the exemplary flow can proceed to step 225 which will be further illustrated below. In another example, the exemplary flow can end at step 260 after providing the guidance data.

However, back in step 210, when the claim processing system determines that the injury in the received electronic medical claim is not a traumatopathic injury, then the "No" branch is taken to step 215.

In step 215, the claim processing system determines when the injury in the received electronic medical claim is one of a plurality of injuries by correlating at least the first three characters of the extracted diagnosis against the description of the injury stored in a table within the diagnosis code database 118, although the claim processing system can use other techniques to determine when the types of injuries. By way of example, types of injuries can include extreme injury or traumatic injury. In this example, extreme injury relates to injury that is life threatening, and traumatic injury relates to a physical injury of sudden onset and severity which require immediate medical attention. Accordingly, when the claim processing system determines that the injury in the received electronic medical claim is neither extreme nor traumatic, then the "No" branch is taken to step 220. The correlation between severity type is performed by validating the diagnosis severity (traumatic, extreme, traumatopathic).

In step 220, the claim processing system provides guidance data to the requesting claims management system 130 indicating that the injury represented by the diagnosis code in the received electronic medical claim is not traumatopathic injury, extreme injury, or traumatic injury, and the exemplary flow can optionally proceed to step 225. In another example, the exemplary flow can proceed to step 260 where the exemplary method ends. In this example, the guidance data can be provided via a graphical user interface to the requesting one of the of claims management system, although the guidance data can be provided using other techniques.

However, back in step 215, when the claim processing system determines that the injury in the received electronic medical claim is either extreme or traumatic, then the Yes branch is taken to step 225.

In step 225, the claim processing system determines when there is one or more historical medical claim(s) data associated with the claimant from the insurance data servers 140 using a unique identification number associated with claimant, although the historical medical claim(s) data can be obtained from other memory locations using other techniques. In this example, each claimant is associated with a unique identification number and the claim processing system searches the plurality of insurance data servers for historical medical claims using the unique identification number, although the claim processing system can use other techniques to identify the historical medical claims. Accordingly, when the claim processing system does not identify any historical medical claim associated with the claimant, then the "No" branch is taken to step 255 where the exemplary method ends after providing guidance data to the requesting one of the plurality of claims management systems 130 indicating that no initial diagnosis code is available for the claimant. However, when the claim processing system determines that there is at least one historical medical claim present for the claimant, then the "Yes" branch is taken to step 230.

In step 230, the claim processing system identifies the initial diagnosis code data present in the obtained historical medical claim(s) by parsing each of the obtained historical medical claim and extracting the initial diagnosis code data present within the initial diagnosis data field, although other techniques can be used to identify the initial diagnosis code.

In step 235, the claim processing system determines when there is a direct clinical correlation between the injury represented by the initial diagnosis code identified in the historical medical claims and the injury represented by the diagnosis code extracted from the received electronic medical claim in step by applying natural language processing technique on the description of the injury associated with the initial diagnosis code and the diagnosis code, although other techniques can be used to identify an direct clinical correlation. In this example, a clinical correlation relates to a process to make a diagnosis on the claimant to treat the injury suffered by the claimant, although clinical correlation can include other types or amounts of information. Additionally, direct clinical correlation relates to a correlation that can be identified without requirement for additional medical data, although correlation can include other types or amounts of information. Further in this example and as illustrated above, the diagnosis code database 118 includes a description of the injury for the diagnosis code extracted from the received electronic claim and similarly, the initial diagnosis code identified in the historical bill also includes a description of the injury that can be obtained either from the diagnosis code database 118 or the insurance data servers 140.

Further, the claim processing system applies natural language processing technique on both description of the injury associated with the initial diagnosis code and the diagnosis code to determine when there is a direct clinical correlation, although other techniques can be used to determine the direct clinical correlation. By way of example, when claimant's historical claim includes an initial diagnosis code M23.203, which represents derangement of unspecified medial meniscus due to old tear or injury, right knee and the diagnosis code in the extracted from the received electronic claim includes the diagnosis code, S83.211A, which represents bucket-handle tear of medial meniscus with a current injury to the right knee as an initial encounter, then the claim processing system can determine a direct clinical correlation. Accordingly, when the claim processing system determines that there is no direct clinical correlation between the injury represented in the initial diagnosis code and the injury represented in the diagnosis code present in the received electronic medical claim, then the No branch is taken to 245 that will be further illustrated below. However, when the claim processing system determines that there is a direct clinical correlation, then the Yes branch is taken to step 240.

In step 240, the claim processing system provides guidance data to the requesting claims management system 130 indicating that there is a direct clinical correlation between the injury in the received electronic medical claim and the injury present in the historical medical claim. Additionally, the claim processing system may also provide the guidance data to reimburse the amount present in the received electronic claim. In this example, the guidance data can be provided via a graphical user interface to the requesting claims management system 130, although the guidance data can be provided using other techniques. Further, the exemplary flow proceeds to step 260 where the exemplary method ends at step 260.

However, back in step 235, when the claim processing system determines that there is no direct clinical correlation between the injury represented by the initial diagnosis code in the historical medical claim and the injury represented by the diagnosis code in the received electronic claim, the "No" branch is taken to step 245.

In step 245, the claim processing system determines when there is an indirect clinical correlation between the injury represented by the initial diagnosis code identified in the historical medical claims and the injury represented by the diagnosis code extracted from the received electronic medical claim by applying natural language processing technique on the description of the injury associated with the initial diagnosis code and the diagnosis code, although other techniques can be used to identify an indirect clinical correlation. In this example, indirect clinical correlation relates to a correlation that can be identified through additional medical data, although indirect clinical correlation can include other types or amounts of information. For example, a database may be developed and maintained by a clinical review team which would review the list of diagnoses to determine the correlation type.

By way of example, if the claimant's historical claim includes an initial diagnosis code F43.12, which represents post-traumatic stress disorder and is categorized as chronic, and the received electronic claim includes a diagnosis code S13.130A which represents subluxation of C2/C3 cervical vertebrae during an initial encounter, then the claim processing system determines indirect clinical correlation.

Accordingly, when the claim processing system determines that there is an indirect clinical correlation between the injury represented by the initial diagnosis code identified in the historical medical claims and the injury represented by the diagnosis code extracted from the received electronic medical claim, then the "Yes" branch is taken to step 250.

In some embodiments, the claim processing system may use a machine learning algorithm when determining the correlation between the injury represented by the initial diagnosis code identified in the historical medical claim and the injury represented by the diagnosis code extracted from the received electronic medical claim. As the system accumulates more records used to train the algorithm, the determinations become more accurate.

Figure 3A:
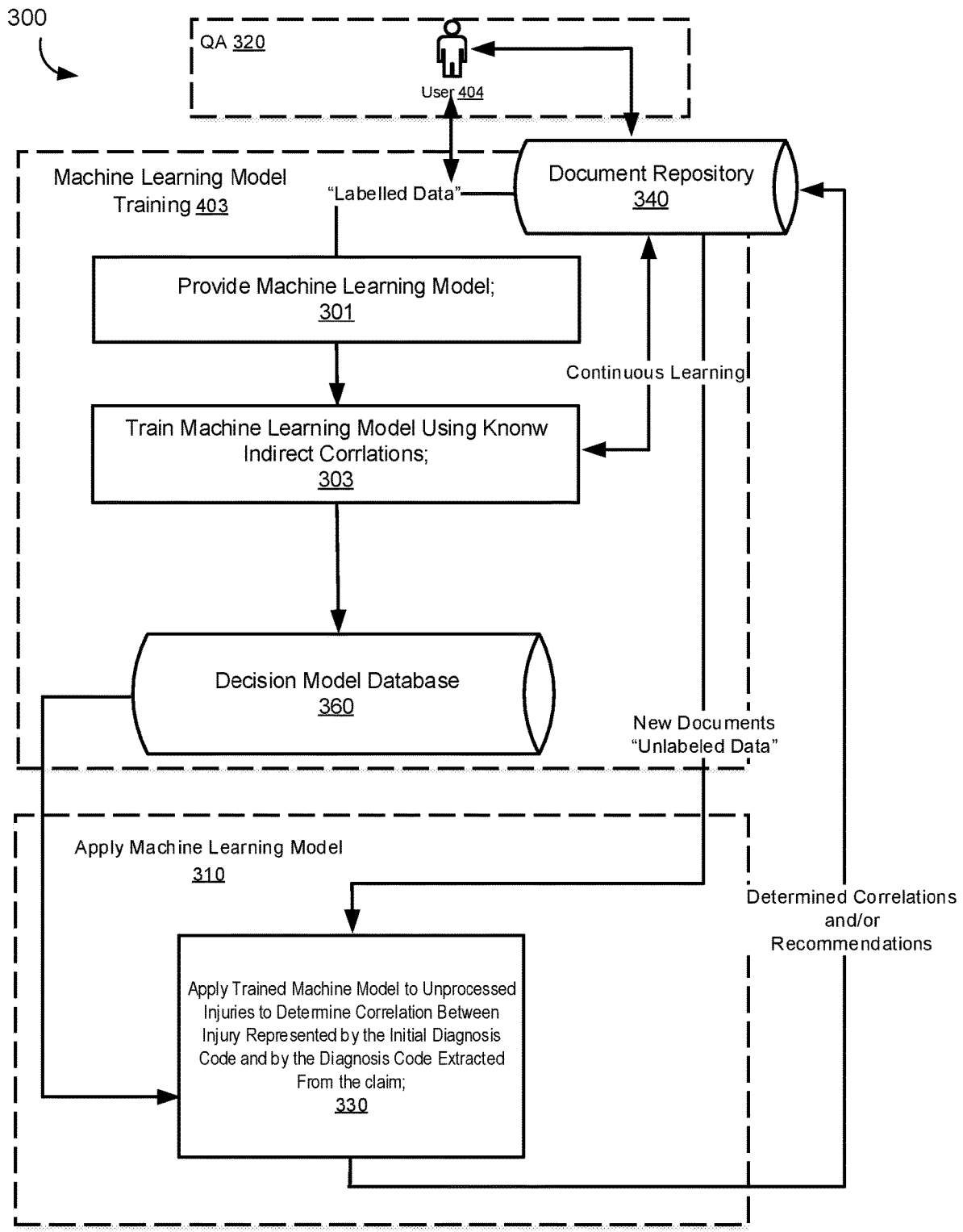
FIGS. 3A-3B illustrate an example training of the machine learning algorithm, according to an implementation of the disclosure.

FIG. 3A illustrates a process 300 for using a machine learning model to determine the indirect correlation between the injury represented by the initial diagnosis code identified in the historical medical claim and the injury represented by the diagnosis code extracted from the received electronic medical claim, according to some embodiments of the disclosed technology. The process 300 may include providing a machine learning model, at 301. The machine learning model may be any machine learning model, algorithm, or an Artificial Intelligence (AI) technique, capable of the functions described herein.

Figure 3B:
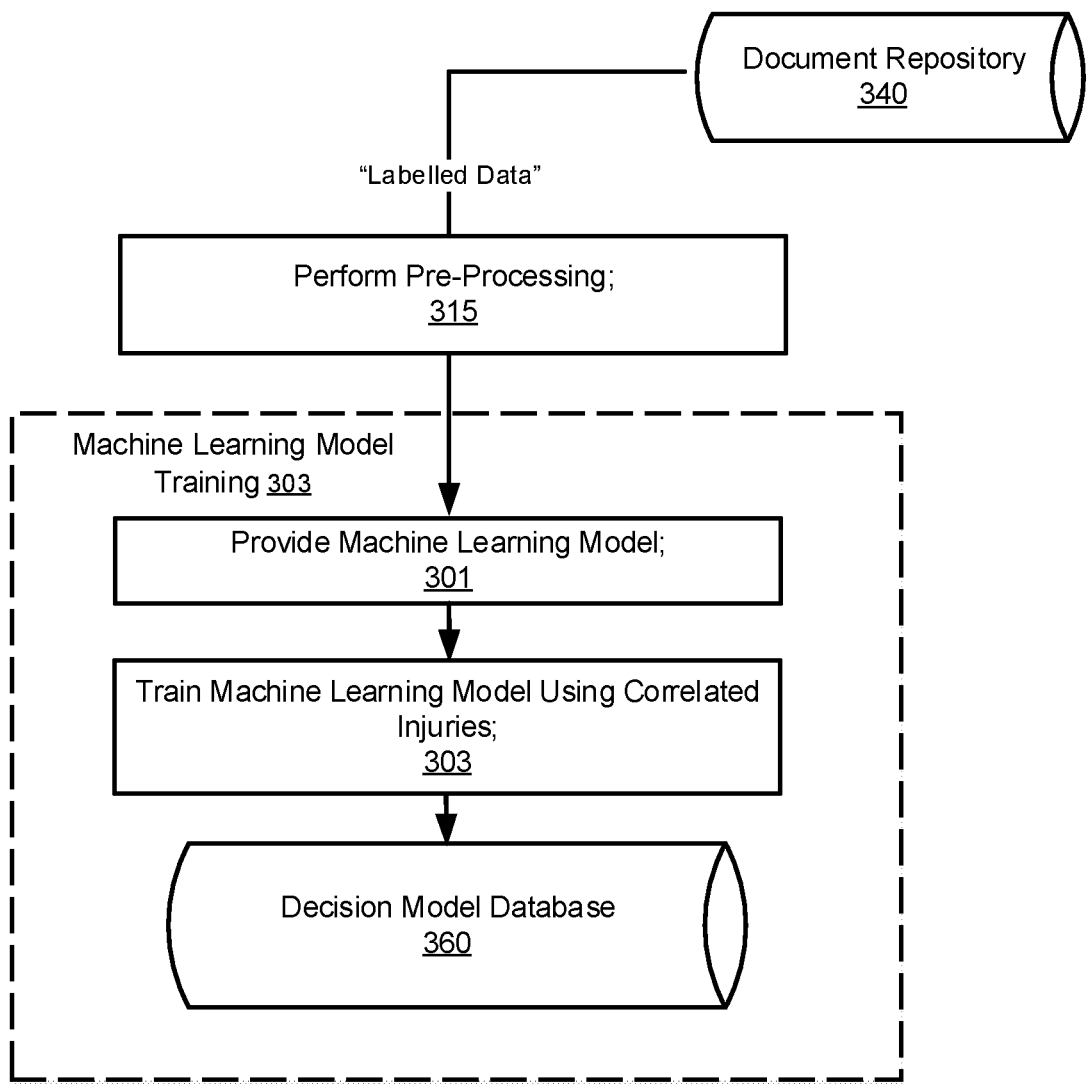

In some embodiments, as illustrated in FIG. 3B, process 300 may include a pre-processing step 315. The pre-processing step 315 may include data preparation and/or data relevancy analysis. For example, pre-processing step 315 may include curating of a corpus (e.g., a collection of processed claim and injury documents) using standard natural language algorithmic techniques such as stemming/lemmatization/stop words/HTML Tags removal/common words and can be achieved using a myriad of Natural Language Processing (NLP) tools (e.g., Beautiful Soup, NLTK, GENSIM, etc.).

Referring back to FIG. 3A, process 300 may include training the machine learning model, at 303. For example, specific keywords, phrases, images, diagnosis code, description of injury, severity level, and/or other data elements, for the previously correlated injuries to claims may be applied as inputs to the machine learning model. Training the machine learning model may include supervised learning, unsupervised learning, or combinations thereof. During the training stage, process 300 may include the machine learning model storing the values related to the decisions made during the training stage in a decision model database 360.

In some embodiments, training the machine learning model 303 may be trained on a document corpus (dataset) provided by document repository 340. For example, the dataset may include a large corpus of injury claim as a raw dataset. Some of the claims may include documents that have been "Labelled" (i.e., documents that that have identified correlations between the injury represented by the initial diagnosis code identified in the historical medical claim and the injury represented by the diagnosis code extracted from the received electronic medical claim).

In some embodiments, training 303 may include using a two-model approach. By virtue of using the two-model approach, results in increased accuracy of process 300. The first model may be used for categorization and data relevancy by using machine learning techniques to first classify data between correlated injuries and uncorrelated injuries. For example, the first model may be performed using feature engineering along with various standard algorithmic ways including, for example, random forest and DNN, based on document titles. By performing the first model step, results in a categorical corpus of labelled as well as unlabeled injures that are specifically related to the claim.

Next, the second model may be applied to the collision-specific corpus of labelled and unlabeled claim documents. For example, the second model may include injury classification model. Specifically, a learned combination of category/sub-category, along with frequency distribution of claim documents, may be obtained from the corpus of labelled document dataset using one or more machine learning algorithms. Here, the category/sub-category may include features related to diagnosis and severity information.

In some embodiments, a threshold may be applied to low frequency combinations resulting in a subset of relevant labelled documents. The subset of relevant labeled documents may be further correlated to the subset of labelled collection of claim documents. The subset of relevant labelled documents may then be split into a train/validate/test data sets in accordance with a split parameter. For example, the subset may be split 80/10/10 between train/validate/test data sets, respectively.

Next, stemming, lemmatization, stop words, and common words techniques may be performed on the subset of relevant labelled documents. For example, this step can be performed by using NLP tools like Beautiful Soup, NLTK, and GENSIM LIBRARY. Next, machine learning classifier may be trained by employing machine learning and AI algorithms (e.g., DNNs, Random forest, etc.) The accuracy of the model may be evaluated during training phase and may be determined by using a train/validate/test dataset. For example, the trained model may result in training loss of 0.16 with accuracy of 90.24%, and a validation loss of 0.19 with accuracy of 89.15%, and test loss of 0.14 with accuracy of 93%.

After training, the machine learning model may be used to associate "unlabeled" data. The machine learning model may utilize the decision data values that are determined to be related to data in the claim and injury documents from a decision model database 360 when determining the new correlations between an unmapped claim and injury documents, at 330. Depending on match reliability, the machine learning model may create accurate correlations for unlabeled claim and injury documents.

Upon receiving a correlated injury claim and injury documents, the mapping tool may apply the identity of the field as an input to the trained machine learning model in, at 330. Responsive to this input, the trained machine learning model may provide the selected match(es) as output with a certain confidence measure.

The process 300 may include the machine learning model providing the correlations, responsive to the provided inputs, at 330. In some embodiments, process 300 may include a quality control phase 320 beginning by user 304 selecting, from document repository 340, association suggestions and/or actual correlations between initial diagnosis injury codes and diagnosis code extracted from the received electronic medical claim determined by the machine learning algorithm and manually verifying the accuracy of the machine learning determination, for examples via the process 200 illustrated in FIG. 2. Those correlations determined by user 304 as inaccurate may be rejected. By contrast, those correlations user 304 deems as accurate or otherwise acceptable may be accepted. In some embodiments, user 304 may complete the correlation process started by the machine learning algorithm. In some embodiments, user 304 accepted correlations from the machine learning algorithm may be further used for relearning and as re-tuning the machine learning model for enhanced accuracy of future predictions.

In cases where associations determined by process 300 are inaccurate, user 304 may manually reject the associated mapping and that rejected correlations may in turn be fed back to the model for further relearning and as re-tuning the machine learning model for enhanced accuracy of future predictions. The relearned model may then be redeployed and utilized again to update and complete the correlations process with enhanced precision.

Referring back to FIG. 2, when the claim processing system determines that there is an indirect clinical correlation between the injury represented by the initial diagnosis code identified in the historical medical claims and the injury represented by the diagnosis code extracted from the received electronic medical claim, then the "Yes" branch is taken to step 250.

In step 250, the claim processing system provides guidance data to the requesting claims management system 130 indicating that there is an indirect clinical correlation between the injury represented by the initial diagnosis code identified in the historical medical claims and the injury represented by the diagnosis code extracted from the received electronic medical claim. Additionally, claim processing system may provide guidance data to the requesting claims management system 130 to request additional medical data to confirm the indirect clinical correlation. The exemplary flow ends at step 260.

However, back in step 245, when the claim processing system determines that there is no indirect clinical correlation between the injury represented by the initial diagnosis code identified in the historical medical claims and the injury represented by the diagnosis code extracted from the received electronic medical claim, then the No branch is taken to step 255.

In step 255, the claim processing system provides guidance data to the requesting one of claims management system 130 indicating that there is no direct clinical correlation or indirect clinical correlation between the between the injury represented by the initial diagnosis code identified in the historical medical claims and the injury represented by the diagnosis code extracted from the received electronic medical claim. Additionally, the claim processing system can also provide guidance data indicating not to reimburse the amount in the received electronic medical claim and the exemplary flow ends at step 260.

Figure 6:
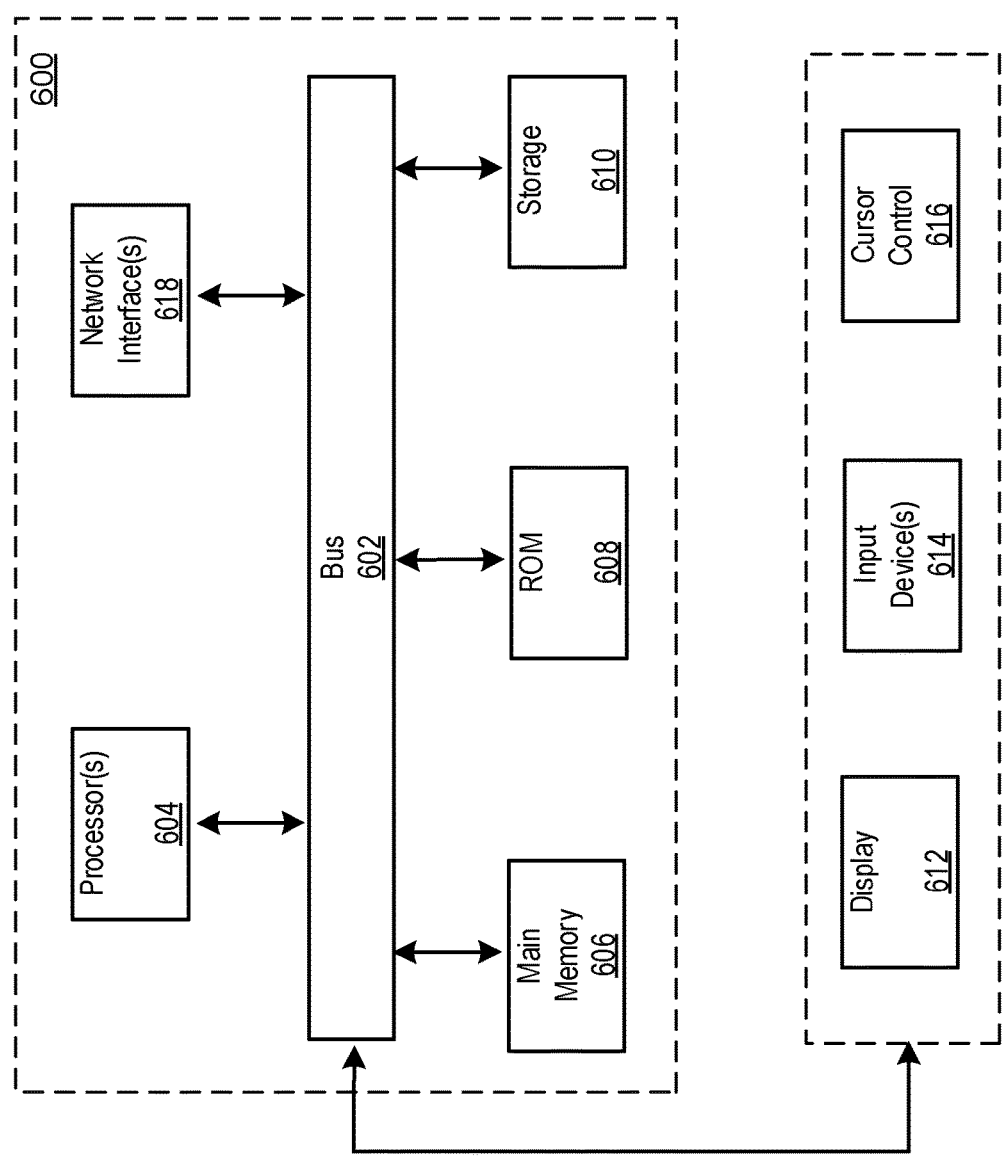
FIG. 6 illustrates an example computing system that may be used in implementing various features of embodiments of the disclosed technology.

Accordingly, this technology provides methods, non-transitory computer readable medium, and apparatuses that assist with more accurately and consistently processing claims than would be possible with a manual review. In particular, examples of the claimed technology are able to extract and correlate data and codes enabling enhanced processing of electronic claims to not only assess provide claim data, but to quantify any injury data to identify the relationship between the current injury and a historical injury. For example, a warning message to the user regarding the migrating diagnosis can prompt a clinical team to request and review claimant health information for clinical relevancy of condition to initial injury. Additionally, Clinical teams may suggest independent medical review, or reports can be run on frequency of migrating diagnosis reported, delta of date of injury, and date of service reported for migrating condition Where components, logical circuits, or engines of the technology are implemented in whole or in part using software, in one embodiment, these software elements can be implemented to operate with a computing or logical circuit capable of carrying out the functionality described with respect thereto. One such example computing module is shown in FIG. 6. Various embodiments are described in terms of this example computing module 600. After reading this description, it will become apparent to a person skilled in the relevant art how to implement the technology using other logical circuits or architectures.

FIG. 6 illustrates an example computing module 600, an example of which may be a processor/controller resident on a mobile device, or a processor/controller used to operate a computing device, that may be used to implement various features and/or functionality of the systems and methods disclosed in the present disclosure.

As used herein, the term module might describe a given unit of functionality that can be performed in accordance with one or more embodiments of the present application. As used herein, a module might be implemented utilizing any form of hardware, software, or a combination thereof. For example, one or more processors, controllers, ASICs, PLAs, PALs, CPLDs, FPGAs, logical components, software routines or other mechanisms might be implemented to make up a module. In implementation, the various modules described herein might be implemented as discrete modules or the functions and features described can be shared in part or in total among one or more modules. In other words, as would be apparent to one of ordinary skill in the art after reading this description, the various features and functionality described herein may be implemented in any given application and can be implemented in one or more separate or shared modules in various combinations and permutations. Even though various features or elements of functionality may be individually described or claimed as separate modules, one of ordinary skill in the art will understand that these features and functionality can be shared among one or more common software and hardware elements, and such description shall not require or imply that separate hardware or software components are used to implement such features or functionality.

Where components or modules of the application are implemented in whole or in part using software, in one embodiment, these software elements can be implemented to operate with a computing or processing module capable of carrying out the functionality described with respect thereto. One such example computing module is shown in FIG. 6. Various embodiments are described in terms of this example-computing module 600. After reading this description, it will become apparent to a person skilled in the relevant art how to implement the application using other computing modules or architectures.

Referring now to FIG. 6, computing module 600 may represent, for example, computing or processing capabilities found within desktop, laptop, notebook, and tablet computers; hand-held computing devices (tablets, PDA's, smart phones, cell phones, palmtops, etc.); mainframes, supercomputers, workstations or servers; or any other type of special-purpose or general-purpose computing devices as may be desirable or appropriate for a given application or environment. Computing module 600 might also represent computing capabilities embedded within or otherwise available to a given device. For example, a computing module might be found in other electronic devices such as, for example, digital cameras, navigation systems, cellular telephones, portable computing devices, modems, routers, WAPs, terminals and other electronic devices that might include some form of processing capability.

Computing module 600 might include, for example, one or more processors, controllers, control modules, or other processing devices, such as a processor 604. Processor 604 might be implemented using a general-purpose or special-purpose processing engine such as, for example, a microprocessor, controller, or other control logic. In the illustrated example, processor 604 is connected to a bus 602, although any communication medium can be used to facilitate interaction with other components of computing module 600 or to communicate externally. The bus 602 may also be connected to other components such as a display 612, input devices 614, or cursor control 616 to help facilitate interaction and communications between the processor and/or other components of the computing module 600.

Computing module 600 might also include one or more memory modules, simply referred to herein as main memory 606. For example, preferably random-access memory (RAM) or other dynamic memory might be used for storing information and instructions to be executed by processor 604. Main memory 606 might also be used for storing temporary variables or other intermediate information during execution of instructions to be executed by processor 604. Computing module 600 might likewise include a read only memory ("ROM") 608 or other static storage device 610 coupled to bus 602 for storing static information and instructions for processor 604.

Computing module 600 might also include one or more various forms of information storage devices 610, which might include, for example, a media drive and a storage unit interface. The media drive might include a drive or other mechanism to support fixed or removable storage media. For example, a hard disk drive, a floppy disk drive, a magnetic tape drive, an optical disk drive, a CD or DVD drive (R or RW), or other removable or fixed media drive might be provided. Accordingly, storage media might include, for example, a hard disk, a floppy disk, magnetic tape, cartridge, optical disk, a CD or DVD, or other fixed or removable medium that is read by, written to or accessed by media drive. As these examples illustrate, the storage media can include a computer usable storage medium having stored therein computer software or data.

In alternative embodiments, information storage devices 610 might include other similar instrumentalities for allowing computer programs or other instructions or data to be loaded into computing module 600. Such instrumentalities might include, for example, a fixed or removable storage unit and a storage unit interface. Examples of such storage units and storage unit interfaces can include a program cartridge and cartridge interface, a removable memory (for example, a flash memory or other removable memory module) and memory slot, a PCMCIA slot and card, and other fixed or removable storage units and interfaces that allow software and data to be transferred from the storage unit to computing module 600.

Computing module 600 might also include a communications interface or network interface(s) 618. Communications or network interface(s) interface 618 might be used to allow software and data to be transferred between computing module 600 and external devices. Examples of communications interface or network interface(s) 618 might include a modem or softmodem, a network interface (such as an Ethernet, network interface card, WiMedia, IEEE 802.XX or other interface), a communications port (such as for example, a USB port, IR port, RS232 port Bluetooth® interface, or other port), or other communications interface. Software and data transferred via communications or network interface(s) 618 might typically be carried on signals, which can be electronic, electromagnetic (which includes optical) or other signals capable of being exchanged by a given communications interface. These signals might be provided to communications interface 618 via a channel. This channel might carry signals and might be implemented using a wired or wireless communication medium. Some examples of a channel might include a phone line, a cellular link, an RF link, an optical link, a network interface, a local or wide area network, and other wired or wireless communications channels.

In this document, the terms "computer program medium" and "computer usable medium" are used to generally refer to transitory or non-transitory media such as, for example, memory 606, ROM 608, and storage unit interface 610. These and other various forms of computer program media or computer usable media may be involved in carrying one or more sequences of one or more instructions to a processing device for execution. Such instructions embodied on the medium, are generally referred to as "computer program code" or a "computer program product" (which may be grouped in the form of computer programs or other groupings). When executed, such instructions might enable the computing module 600 to perform features or functions of the present application as discussed herein.

Various embodiments have been described with reference to specific exemplary features thereof. It will, however, be evident that various modifications and changes may be made thereto without departing from the broader spirit and scope of the various embodiments as set forth in the appended claims. The specification and figures are, accordingly, to be regarded in an illustrative rather than a restrictive sense.

Although described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the present application, whether or not such embodiments are described and whether or not such features are presented as being a part of a described embodiment. Thus, the breadth and scope of the present application should not be limited by any of the above-described exemplary embodiments.

Terms and phrases used in the present application, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

What is claimed is:

1. A method comprising:
obtaining a database comprising correlations between conditions having diagnosis codes, the correlations indicating whether a current condition is not caused by, caused by, or associated with a traumatic incident associated with a historical condition;
receiving a first electronic medical claim associated with a first claimant;
determining whether historical claim data includes a historical medical claim associated with the first claimant; and
responsive to determining the historical claim data includes the historical medical claim associated with the first claimant, providing the historical medical claim and the first electronic medical claim as input to one or more trained machine learning models, wherein responsive to the input, at least one of the trained machine learning models outputs one of the correlations between a condition associated with the first electronic medical claim and a condition associated with the historical medical claim, wherein the one or more trained machine learning models have been trained using the correlations in the database.

2. The method of claim 1, wherein the condition associated with the historical medical claim specifies historical claim data for the first claimant.

3. The method of claim 1, further comprising providing, when the correlation is absent, claim processing guidance data relating to absence of correlation between the condition associated with the first electronic medical claim and the condition associated with the historical medical claim.

4. The method of claim 1, wherein the first electronic medical claim comprises an electronic casualty claim and the diagnosis codes include training at least one ICD code.

5. The method of claim 1, further comprising analyzing by a data processor training at least one of the diagnosis codes to determine a severity of the condition associated with the historical medical claim.

6. The method of claim 1, further comprising:
training the one or more machine learning models using the correlations in the database.

7. A system, comprising:
a processor;
a memory coupled to the processor; wherein the processor is configured to:
obtain a database comprising correlations between conditions having diagnosis codes, the correlations indicating whether a current condition is not caused by, caused by, or associated with a traumatic incident associated with a historical condition;
receive a first electronic medical claim associated with a first claimant;
determine whether historical claim data includes a historical medical claim associated with the first claimant; and
responsive to determining the historical claim data includes the historical medical claim associated with the first claimant, provide the historical medical claim and the first electronic medical claim as input to one or more trained machine learning models, wherein responsive to the input, at least one of the trained machine learning models outputs one of the correlations between a condition associated with the first electronic medical claim and a condition associated with the historical medical claim, wherein the one or more trained machine learning models have been trained using the correlations in the database.

8. The system of claim 7, wherein the condition associated with the historical medical claim specifies historical claim data for training the first claimant.

9. The system of claim 7, wherein the processor is further configured to provide, when the correlation is absent, claim processing guidance data relating to absence of correlation between the condition associated with the first electronic medical claim and the condition associated with the historical medical claim.

10. The system of claim 9, wherein the processor is further configured to analyze training at least one of the diagnosis codes to determine a severity of the condition associated with the historical medical claim.

11. The system of claim 7, wherein the first electronic medical claim comprises an electronic casualty claim and the diagnosis codes include training at least one ICD code.

12. The system of claim 7, wherein the processor is configured to:
train the one or more machine learning models using the correlations in the database.

13. A non-transitory computer-readable storage medium storing a plurality of instructions executable by one or more processors, the plurality of instructions when executed by the one or more processors cause the one or more processors to:
obtain a database comprising correlations between conditions having diagnosis codes, the correlations indicating whether a current condition is not caused by, caused by, or associated with a traumatic incident associated with a historical condition;
receive a first electronic medical claim associated with a first claimant;
determine whether historical claim data includes a historical medical claim associated with the first claimant; and
responsive to determining the historical claim data includes the historical medical claim associated with the first claimant, provide the historical medical claim and the first electronic medical claim as input to one or more trained machine learning models, wherein responsive to the input, at least one of the trained machine learning models outputs one of the correlations between a condition associated with the first electronic medical claim and a condition associated with the historical medical claim, wherein the one or more trained machine learning models have been trained using the correlations in the database.

14. The non-transitory computer readable medium of claim 10, wherein the condition associated with the historical medical claim specifies historical claim data for training the first claimant.

15. The non-transitory computer readable medium of claim 13, wherein the processor is further configured to provide, when the correlation is absent, claim processing guidance data relating to absence of correlation between the condition associated with the first electronic medical claim and the condition associated with the historical medical claim.

16. The non-transitory computer readable medium of claim 10, wherein the first electronic medical claim comprises an electronic casualty claim and the diagnosis codes include training at least one ICD code.

17. The non-transitory computer readable medium of claim 10, wherein the processor is further configured to analyze training at least one of the diagnosis codes to determine a severity of the condition associated with the historical medical claim.

18. The non-transitory computer readable medium of claim 13, wherein the processor is further configured to:
train the one or more machine learning models using the correlations in the database.

* * * * *